(12) United States Patent
Gordon

(10) Patent No.: US 11,801,142 B2
(45) Date of Patent: Oct. 31, 2023

(54) NON-INVASIVELY ADJUSTABLE BONE PROSTHESIS

(71) Applicant: Jeffrey David Gordon, Phoenixville, PA (US)

(72) Inventor: Jeffrey David Gordon, Phoenixville, PA (US)

( * ) Notice: Subject to any disclaimer, the term of this patent is extended or adjusted under 35 U.S.C. 154(b) by 168 days.

(21) Appl. No.: 16/569,277

(22) Filed: Sep. 12, 2019

(65) Prior Publication Data

US 2021/0077260 A1 Mar. 18, 2021

(51) Int. Cl.
*A61F 2/30* (2006.01)
*A61F 2/36* (2006.01)
*A61F 2/38* (2006.01)
A61B 17/74 (2006.01)
A61F 2/48 (2006.01)

(52) U.S. Cl.
CPC ........ *A61F 2/30749* (2013.01); *A61F 2/3662* (2013.01); *A61F 2/3859* (2013.01); *A61B 17/74* (2013.01); *A61F 2/48* (2021.08); *A61F 2002/3052* (2013.01); *A61F 2002/3055* (2013.01); *A61F 2002/30405* (2013.01); *A61F 2002/30522* (2013.01); *A61F 2002/30706* (2013.01)

(58) Field of Classification Search
CPC ........ A61F 2/3662; A61F 2/3859; A61F 2/48; A61F 2002/30405; A61F 2002/3052; A61F 2002/30522; A61F 2002/3055; A61F 2002/30706; A61F 2002/30734; A61F 2002/30736; A61F 2/30; A61B 17/7216
See application file for complete search history.

(56) References Cited

U.S. PATENT DOCUMENTS 2,649,076 A * 8/1953 Dupre ............... F01B 17/00
 91/410
4,384,373 A * 5/1983 Sivash .............. A61F 2/3845
 623/23.45

* cited by examiner

*Primary Examiner* — Christopher D. Prone

(57) ABSTRACT

The invention herein described is an endoprosthesis intended to replace a resected portion of bone and joint. The invention can be non-invasively, manually operated to lengthen a patient's limb both intraoperatively and postoperatively. It includes bone anchoring components for anchoring to a first and second long bone, a joint to replace the function of an orthopedic joint, and a purely mechanical lengthening mechanism which can be located and operated manually by an operator by pressing on skin of a patient without requiring a surgical incision. An alternative embodiment of the invention describes a similar extendable endoprosthesis which is unlocked by an operator by pressing on skin of a patient and the limb is subsequently pulled or pushed by the operator to change its length. The invention does not need or include any magnets, electric motors, electric current, application of heat or a fluid displacement (hydraulic) system.

16 Claims, 19 Drawing Sheets

NON-INVASIVELY ADJUSTABLE BONE PROSTHESIS

This application claims benefit of Provisional Patent Application: 62/766,481 "Non-Invasively Adjustable Bone Prosthesis" Filing date: Oct. 22, 2018 by Jeffrey David Gordon

BACKGROUND OF THE INVENTION

Limb salvage is a surgical procedure that replaces a diseased or otherwise damaged bone and reconstructs a functional limb using an implant. In many cases the implant includes a replacement for a resected joint such as the knee or hip. Osteosarcoma and extreme traumatic injury are examples of circumstances where limb salvage may be required. If the patient is a child or adolescent the operative limb will need to be gradually lengthened as he or she grows to maintain leg length equality with the contralateral limb. Historically, multiple surgeries have been required to periodically lengthen the implant until the patient reaches skeletal maturity, but multiple surgeries is not an optimal solution. The incidence of infection increases by about 5% with each successive surgery. For example, a patient requiring 10 lengthening procedures will have approximately 50% greater risk of infection than a patient who does not require lengthening surgery.

Magnetically actuated implants (U.S. Pat. No. 6,849,076) have been developed so that lengthening can be achieved without the need for surgery. These implants have demonstrated clinical success, but they have disadvantages. The transmission of torque to the implant from an external magnet is a difficult engineering challenge. The magnet located in the implant is small and the magnet located outside the patient is significantly far from the implant. Since magnetic attraction decreases exponentially with increasing distance between magnets, very large gear reduction is necessary to generate the force required to lengthen the implant from a small torque. Extensive gear reduction mechanisms located within the implant have been required, adding cost and potential for mechanical failure. These intricate implants are not able to withstand the hammering required to be seated by press fit and therefore are typically cemented into place. In addition, magnetic implants preclude MRI imaging.

Motorized extendable implants (U.S. Pat. No. 5,961,553) have been proposed wherein a small electric motor, powered by a battery or an inductive electric source, is used to turn a lead screw to lengthen the implant. Again, these are complicated implants that risk mechanical failure or clinical failure, wherein the implant is unable to generate force required for lengthening.

Hydraulically extendable implants (U.S. Pat. No. 5,350,379) have been described wherein a fluid pump is activated by manually pushing a patient's skin, an internal electric fluid pump is controlled by an external system, or an external fluid pump is connected percutaneously to the implant. Hydraulic seals are prone to failure and the overall device can be imprecise. Percutaneous systems significantly increase the risk of infection. A more simplified, robust solution is needed which does not rely on magnets, an electric motor, or hydraulics.

SUMMARY OF THE INVENTION

The proposed invention solves the problems mentioned above. The implant is made from traditional implantable materials; no magnetic materials are necessary. The invention is purely mechanical and operable with non-invasive, direct, manual manipulation of the implant by pressing on the patient's skin, so no motors or hydraulic systems are needed. In the case of a distal femur replacement, the most common need for osteosarcoma patients, this manipulation occurs at the medial and lateral surfaces of the knee joint at the site where the femoral condyles were located prior to resection. Implantation of a distal femur replacement typically requires an incision along the axis of the femur in the coronal plane and the skin at the medial and lateral aspects of the knee is left intact. So manual manipulation of the implant should not interfere with wound healing or cause pain at the site of the surgical incision. Furthermore, a safety device is presented here to help prevent inadvertent lengthening. The safety device requires exact rotational orientation of the joint, preferably somewhat flexed so that the limb is free from body weight loads, before length adjustment can be achieved. In the event that a patient happens to have their joint in this exact rotational orientation and also inadvertently pushes the actuation mechanism, the preferred embodiment would require repeated manual manipulation not just on one side but coordinated manipulation from both sides of the joint—which should not occur accidentally. While distal femur and proximal tibia replacement implants are presented here, it will be obvious to those familiar with endoprostheses that this invention could be adapted for the distal humerus. In addition to cases of osteosarcoma resection, the implant presented here can be utilized for any condition requiring bone resection and replacement with a prosthesis—such as traumatic injuries, injuries to the growth plate, congenital or developmental deformities or any other condition requiring postoperative lengthening.

DESCRIPTION OF THE EMBODIMENTS OF THE INVENTION

The following description of the preferred embodiment(s) is merely exemplary in nature and is in no way intended to limit the invention, its application, or uses. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Figure 1:
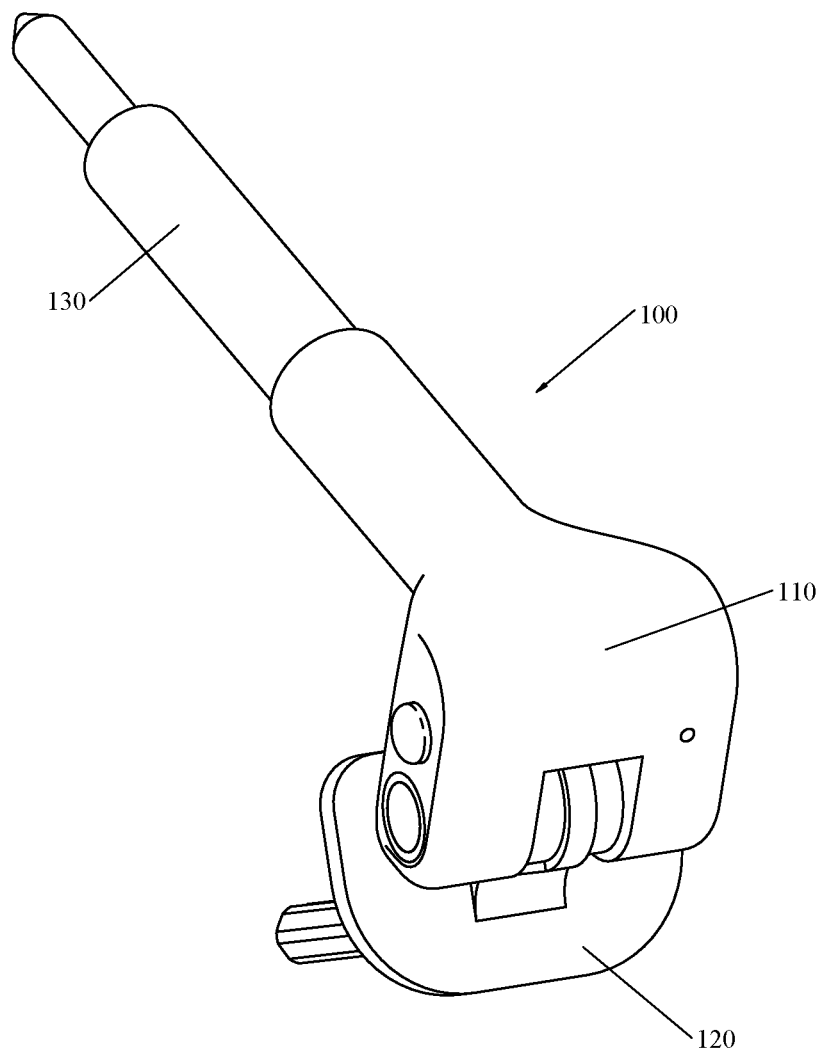
FIG. 1 is a perspective view of a first embodiment of the invention.
Figure 2:
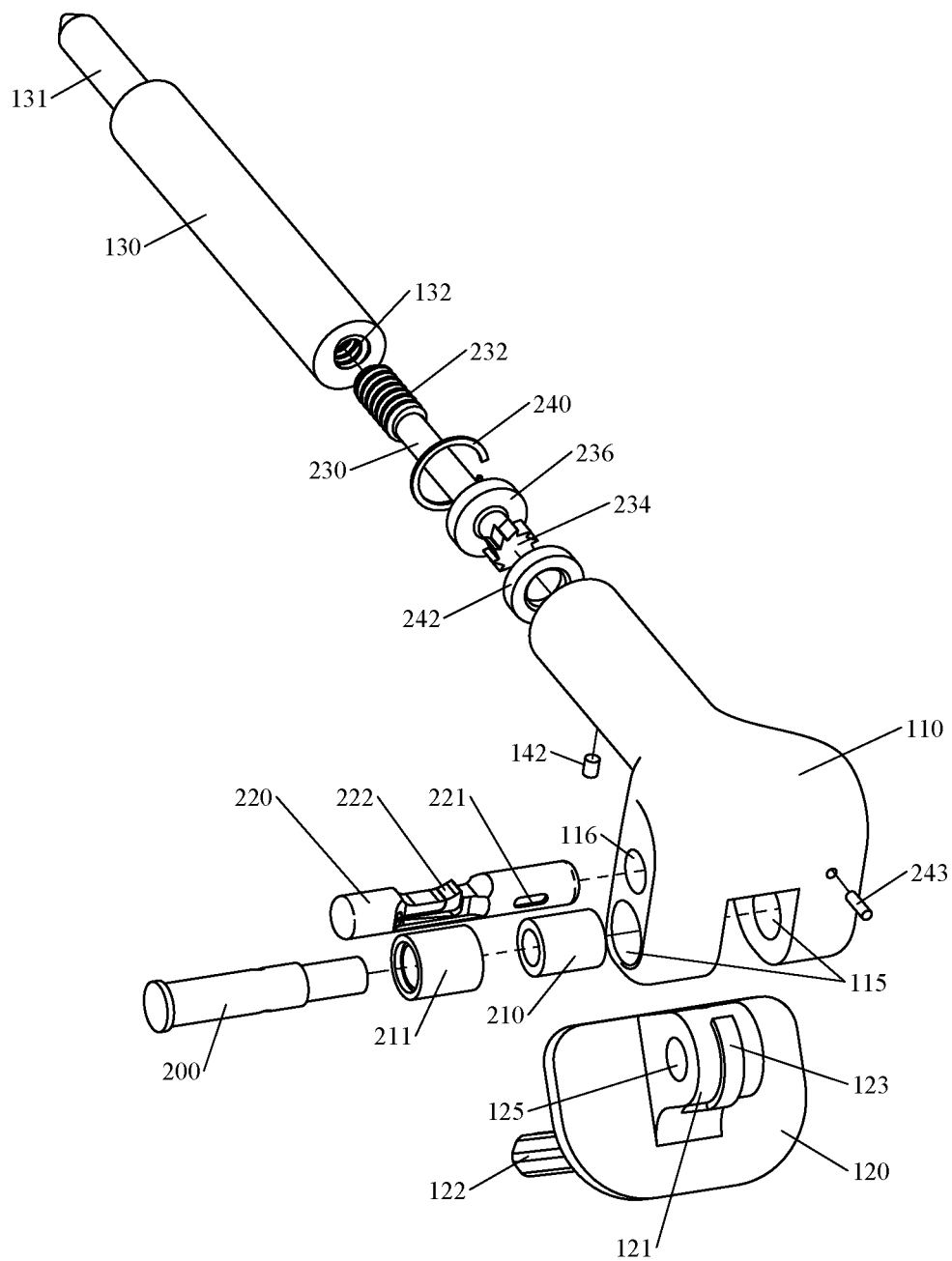
FIG. 2 is an exploded, perspective view of a first embodiment of the invention.
Figure 4:
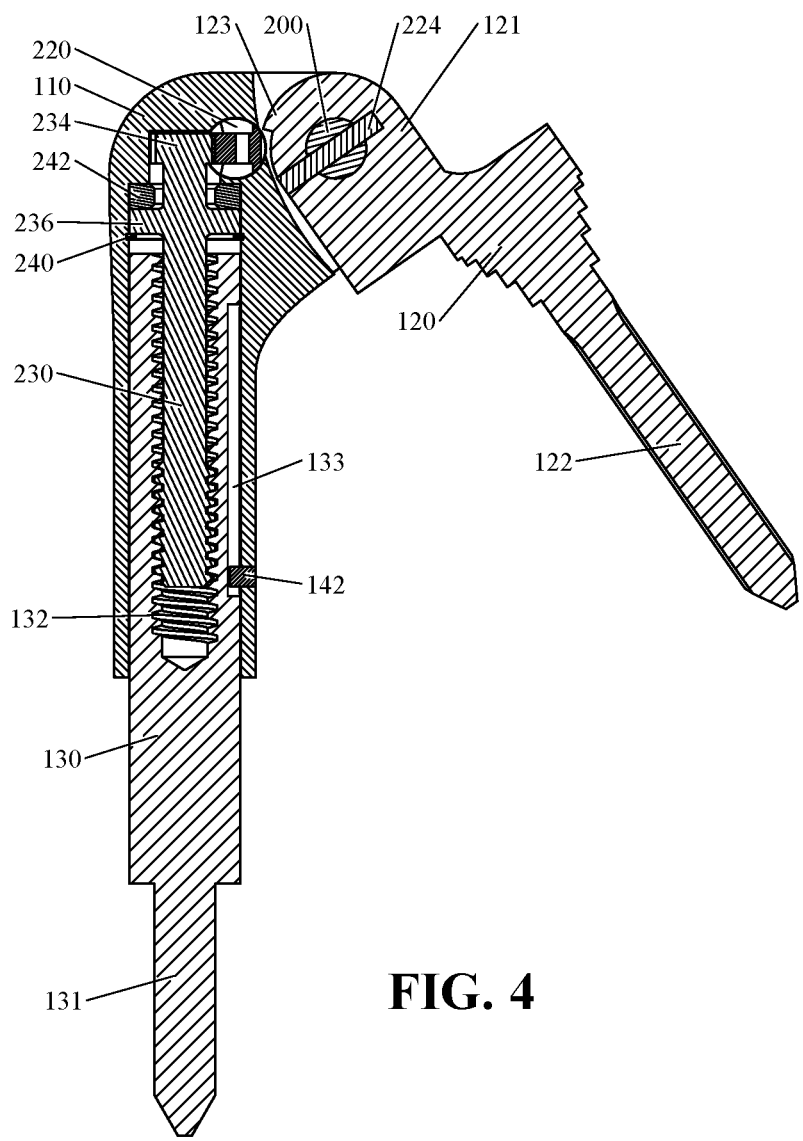
FIG. 4 is a sectional view of a first embodiment of the invention.
Figure 3:
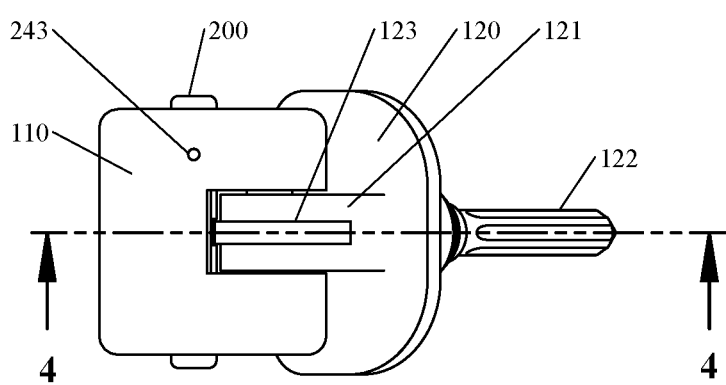
FIG. 3 is a rotated front view of a first embodiment of the invention.
Figure 5:
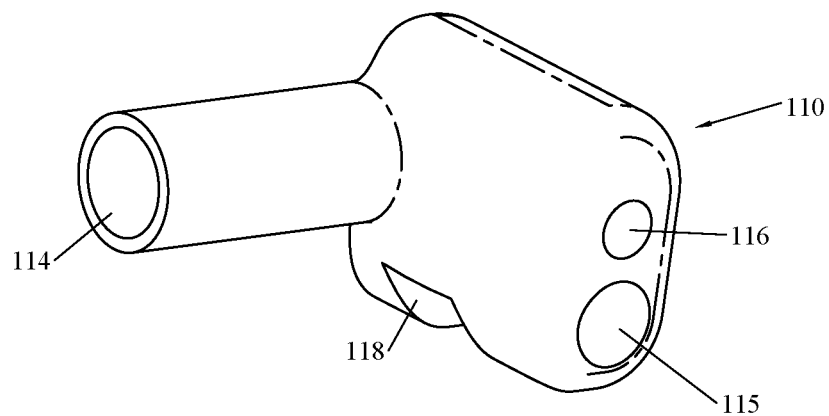
FIG. 5 is a reverse angle view of a distal femur component.
Figure 6:
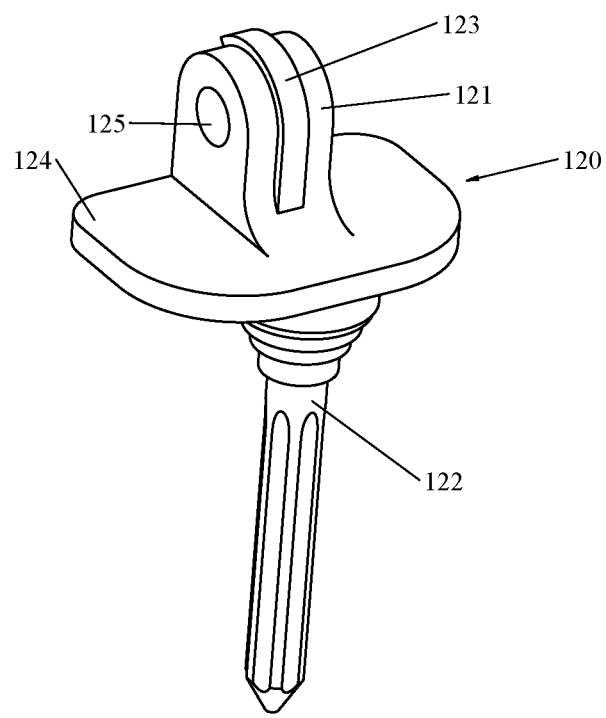
FIG. 6 is a perspective view of a tibial component.

FIG. 1 shows the preferred embodiment of the invention 100 configured for distal femur replacement with the knee joint positioned in a flexed orientation. It consists generally of a distal femur component 110, a femoral shaft component 130, and a tibial component 120. FIG. 2 shows an exploded view, FIG. 3A is a side view and FIG. 3B is a sectional view of the same embodiment and configuration of the invention to clarify the operation of the interior components. FIGS. 4 & 5 are isolated views of distal femur component 110 and tibial component 120 respectively. Femoral shaft component 130 has an intramedullary stem 131 meant to be inserted into the intramedullary canal of the patient's femur after resection of the distal portion of the femur. Attachment of femoral shaft component 130 to the patient's bone is preferably aided by a porous surface into which bone can grow. Also, a surface application of hydroxyapatite or biological cells may be included to aid bone connection. Alternatively, bone cement may be used for attachment. In practice, femoral shaft component 130 may be two separate, but connectable, parts so that intramedullary stem 131 may remain in place in the event that another portion of the implant needs to be surgically replaced. Femoral shaft component 130 also has a threaded bore 132 to receive a leadscrew 230 which has threads 232 matched to mate with threaded bore 132. Threads may be standard machine threads, or trapezoidal, acme or square threads for improved strength. Lead screw 230 also has a boss 236 and a ratchet 234. A bushing 242 is slid over ratchet 234 until it abuts boss 236 and then this subassembly is fully inserted into a bore 114 (see FIG. 4) in distal femur component 110 and retained there with a retaining ring 240 so that lead screw 230 is able to rotate within distal femur component 110, but will not translate. A pin 142 is pressed into distal femur component 110 and rides in a slot 133, thereby retaining, preventing relative rotation, and limiting travel of femoral shaft component 130 within distal femur component 110. A shaft 220 is slid into a bore 116 which passes completely through distal femur component 110. A pin 243 is pressed into a hole in distal femur component 110 to ride in a slot 221 in shaft 220, thereby retaining shaft 220 within distal femur component 110, maintaining its rotational alignment, and limiting its linear travel. Tibial component 120 consists of a plateau 124, a stem 122, and a boss 121 with a lockout protrusion 123 and a bore 125. Tibial component 120 is attached to distal femur component 110 with an axle 200 which rotates within bushings 210 and 211 which are preferably made from a low friction material such as cross-linked UHMWPE (ultra-high molecular weight polyethylene) or PEEK (polyether ether ketone). Bore 125 is aligned with an axle bore 115 in distal femur component 110 in which bushings 210 and 211 have been inserted. When placed in this position, boss 121 fits in a slot 118 in distal femur component 110. Axle 200 is then slid through bushing 211, bore 125, bushing 210 and is rigidly attached to tibial component 120 with a pin 224. The attachment of distal femur component 110 to tibial component 120 is preferably done intraoperatively.

Figure 7:
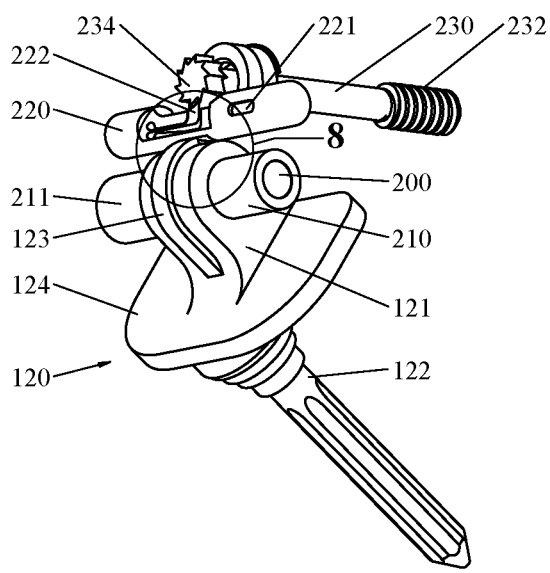
FIG. 7 is a perspective view of the lengthening mechanism, shown isolated from its housing.
Figure 8:
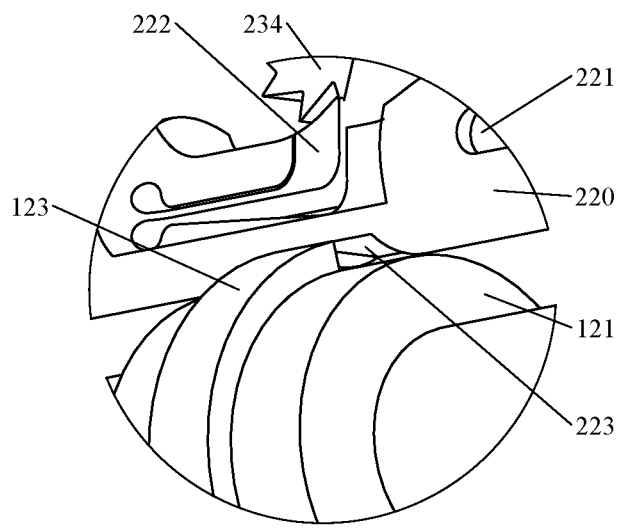
FIG. 8 is an enlarged view of the lengthening mechanism.
Figure 9:
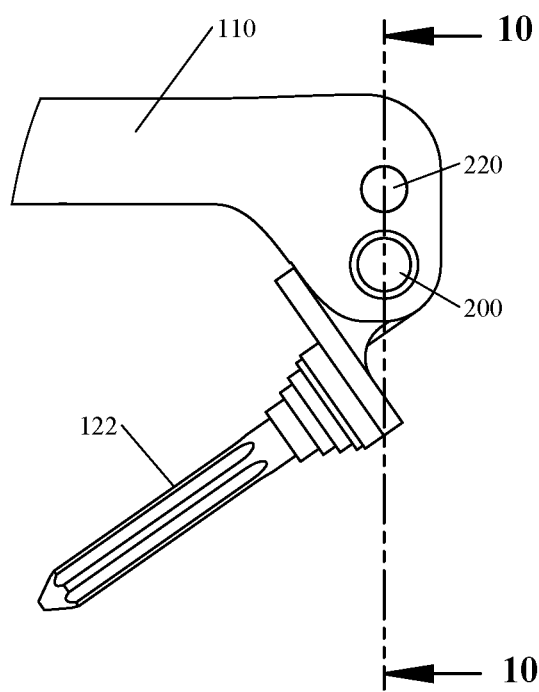
FIG. 9 is a side view of a first embodiment of the invention.
Figure 10:
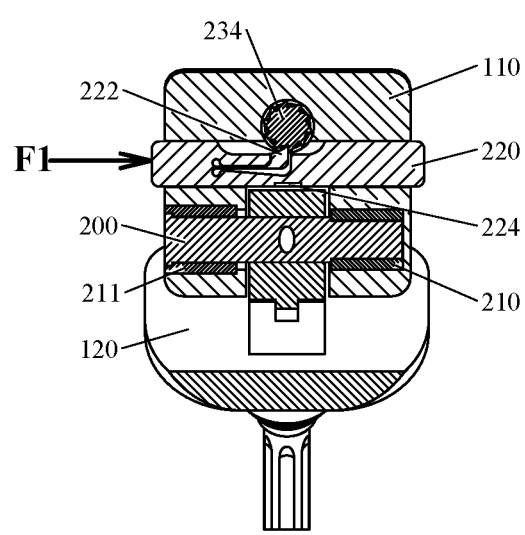
FIG. 10 is a sectional view of a first embodiment of the invention.
Figure 11:
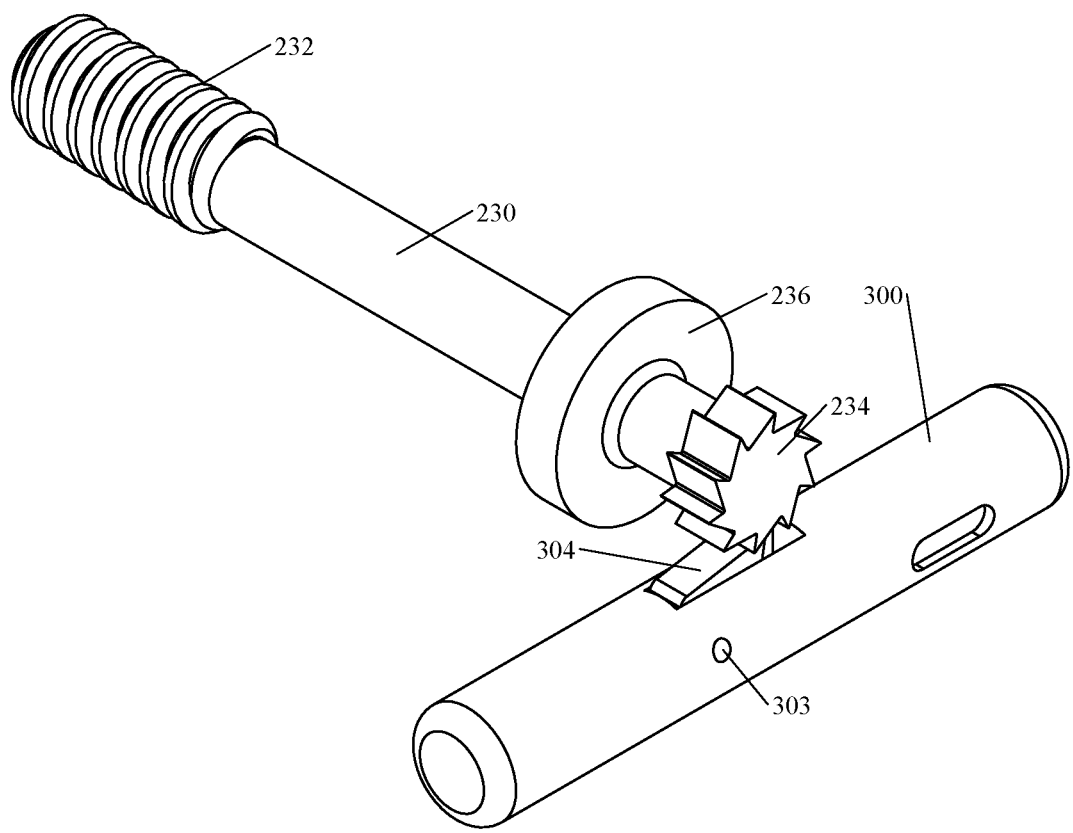
FIG. 11 is a perspective view a ratchet and pawl mechanism, shown isolated from its housing.
Figure 12:
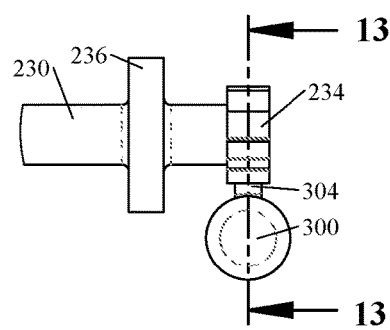
FIG. 12 is a side view of a ratchet and pawl mechanism.

The interaction of shaft 220 and lead screw 230 as well as the interaction of shaft 220 and lockout protrusion 123 is illustrated in FIGS. 7 & 8 wherein the lengthening mechanism is shown removed from distal femur component 110. Sectional view FIG. 10 also illustrates the function of the lengthening mechanism. Shaft 220 includes a thin serpentine cut which creates a flexure (compliant mechanism) so that a flexible pawl 222 is created. When shaft 220 is pushed to the right with a force F1 as shown in FIG. 10 flexible pawl 222 will push a tooth of ratchet 234 and thereby rotate leadscrew 230 counterclockwise. Due to the threaded connection between leadscrew 230 and femoral shaft component 130, this rotation will translate femoral shaft 130 so that it moves out of bore 114 in distal femur component 110, thereby lengthening the implant. However, when shaft 220 is pushed back to the left, flexible pawl 222 will contact the sloped side of a tooth of ratchet 234 and will flex out of the way and will not rotate ratchet 234. The interaction of flexible pawl 222 and ratchet 234 is effectively a one-way clutch. Repeatedly pushing shaft 220 back and forth will gradually lengthen the implant until a satisfactory length is achieved. The length of the patient's femur can be measured with fluoroscope, x-ray, or a measuring device such as a caliper or ruler. The purpose of lockout protrusion 123 in tibial component 120 is also illustrated in FIGS. 7 & 8. When tibial component 120 is oriented as shown shaft 220 is able to translate without collision. However if the patient's tibia (and therefore tibial component 120) is rotated to a more extended knee position then lockout protrusion 123 will occupy the space created by slot 223, thereby preventing shaft 220 from translating. The purpose of lockout protrusion 123 is to prevent inadvertent translational motion of shaft 220 and subsequent advancement of the lengthening mechanism of the invention. It will be straightforward to envision that lockout protrusion 123 could be made to allow translation of rack 220 at virtually any rotational orientation of the tibia simply by changing the shape of the protrusion.

Figure 13:
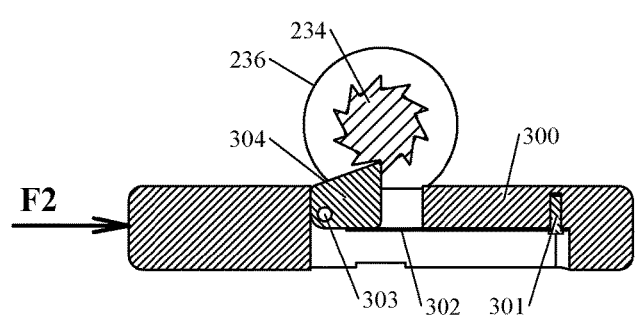
FIG. 13 is a sectional view of a ratchet and pawl mechanism in a driving configuration.
Figure 14:
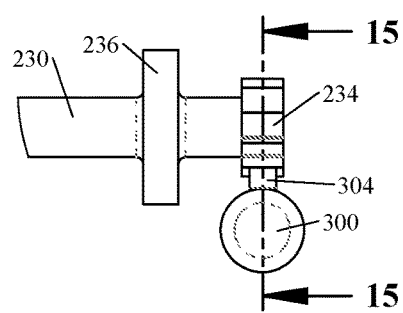
FIG. 14 is a side view of a ratchet and pawl mechanism.
Figure 15:
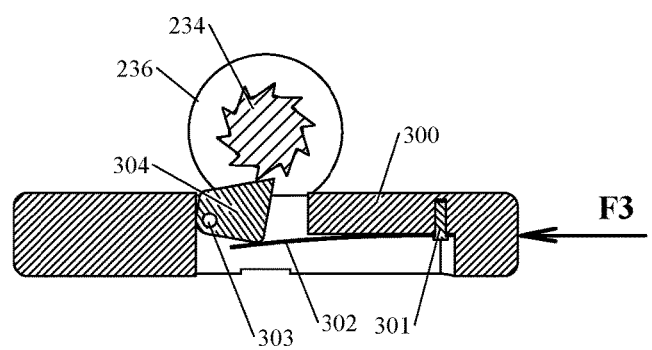
FIG. 15 is a sectional view of a ratchet and pawl mechanism in a freewheeling configuration.

FIGS. 11 through 15 illustrate an alternative embodiment of the lengthening mechanism wherein a shaft 300 includes a pawl 304 which can rotate on an axle 303. A leaf spring 302, which is attached to shaft 300 with a pin 301, pushes pawl 304 into a driving position. As shaft 300 is pushed to the right with force F2 as shown in FIG. 13 pawl 304 pushes a tooth of ratchet 234, thereby rotating ratchet 234 counterclockwise. After rack 300 reaches full travel, pushing it back to the left with force F3 as shown in FIG. 15 causes pawl 304 to contact the sloped edge of a tooth of ratchet 234 which causes pawl 304 to rotate down—which in turn flexes leaf spring 302. Once pawl 304 is clear of ratchet 234, leaf spring 302 pushes pawl 304 back to the driving position. The function of this embodiment is identical to the function of the previous embodiment: it is a one-way clutch.

Figure 16:
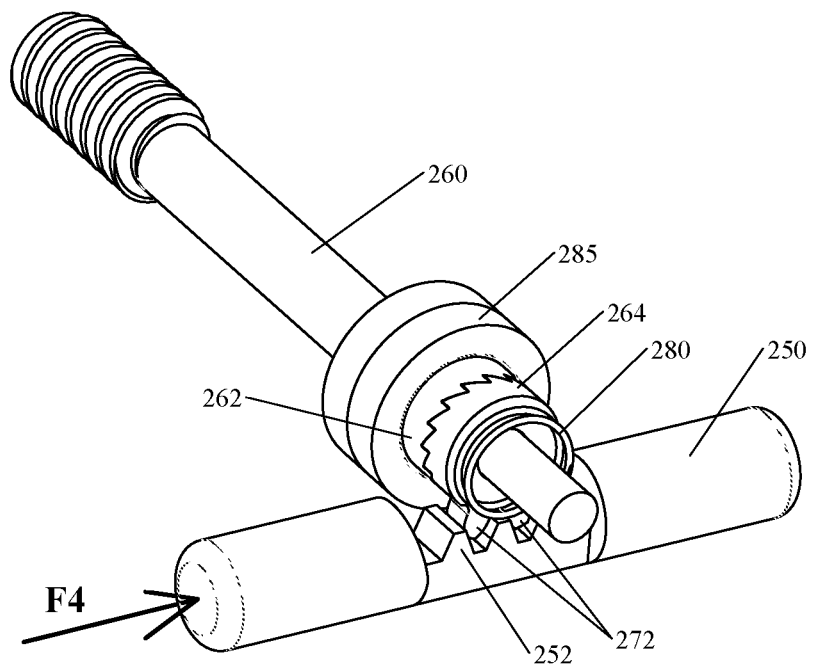
FIG. 16 is a perspective view of a rack and pinion mechanism shown isolated and in a driving configuration.
Figure 17:
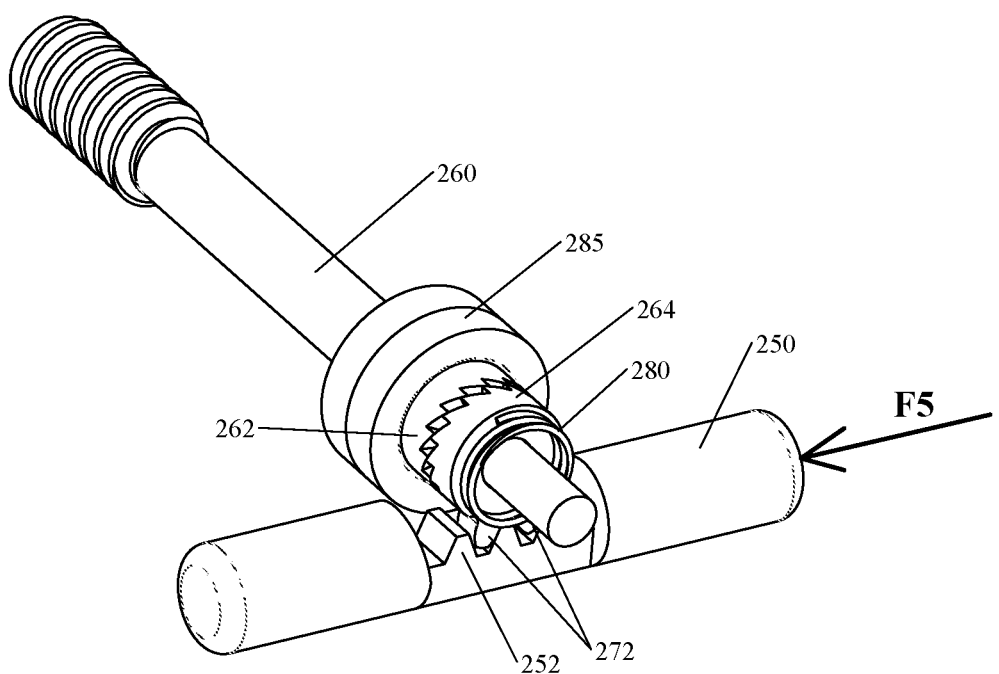
FIG. 17 is a perspective view of a rack and pinion mechanism shown isolated and in a freewheeling configuration.

FIGS. 16 & 17 illustrate an alternative embodiment of a one-way clutch. In this embodiment a clutch plate 264 has ratchet teeth that interdigitate with communicating ratchet teeth on a clutch rotor 262. A spring 280 maintains the engagement of the teeth. When the teeth are engaged as shown in FIG. 16 and a rack 250 with rack teeth 252 is pushed to the right with a force F4 as shown, then corresponding gear teeth 272 on clutch plate 264 will rotate counterclockwise which will also rotate a leadscrew 260, thereby lengthening the overall device. When rack 250 is pushed back to the left with a force F5 as shown in FIG. 17 rack teeth 252 will rotate gear teeth 272 and thereby rotate clutch plate 264 clockwise. However the ratchet teeth on clutch plate 264 and clutch rotor 262 will disengage as spring 280 compresses and clutch plate 264 will simply freewheel.

Figure 18:
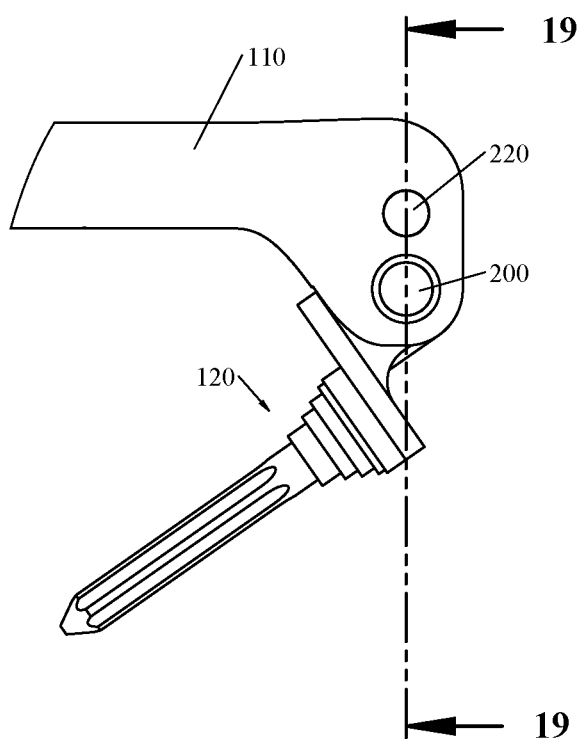
FIG. 18 is a side view of the invention with a spring-return.
Figure 19:
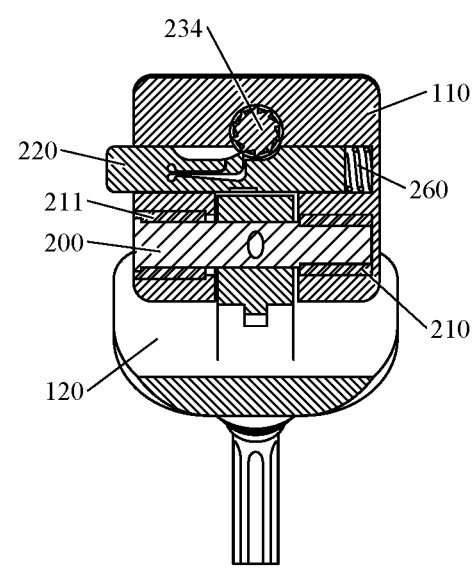
FIG. 19 is a sectional view of the invention with a spring-return.

FIGS. 18 & 19 illustrate an alternative embodiment of the invention where a return spring 260 is implemented to return shaft 220 to its initial configuration after it has been depressed. If there is not access to both sides of the implant, this configuration can be used instead of the previously illustrated versions. As an example, a distal tibia replacement might only allow access at the lateral aspect of the ankle since the fibula may block access to the medial side.

Figure 20:
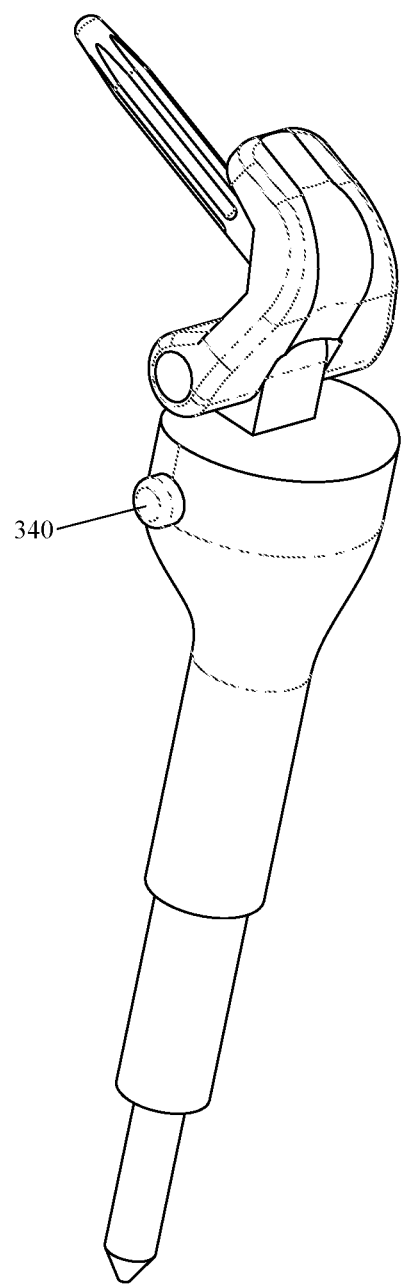
FIG. 20 is a perspective view of the invention which is configured to replace a proximal tibia.
Figure 21:
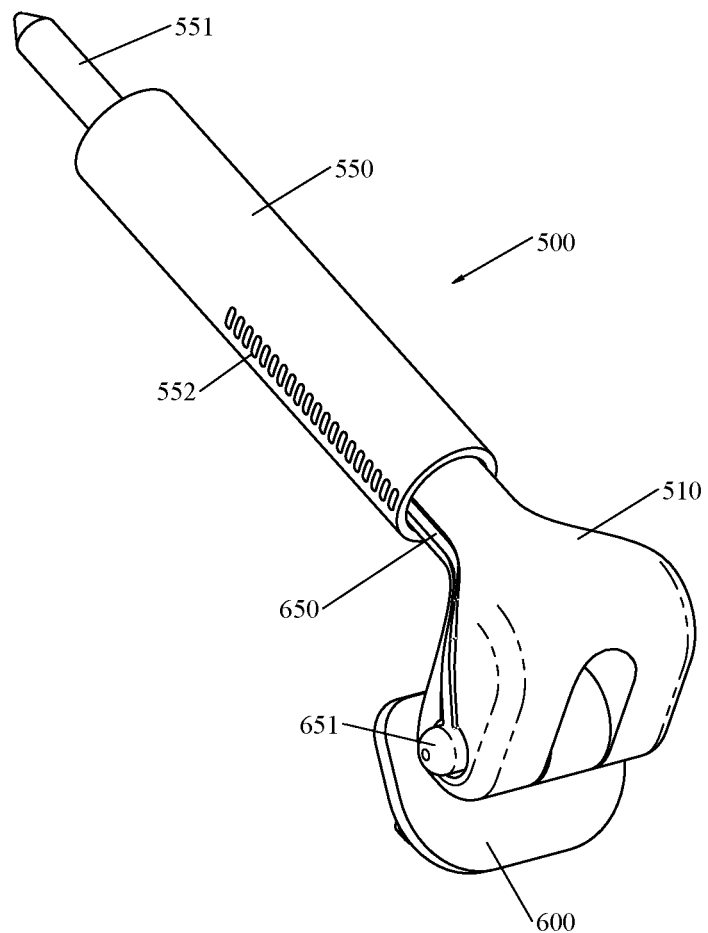
FIG. 21 is a perspective view of an alternative embodiment of the invention.
Figure 22:
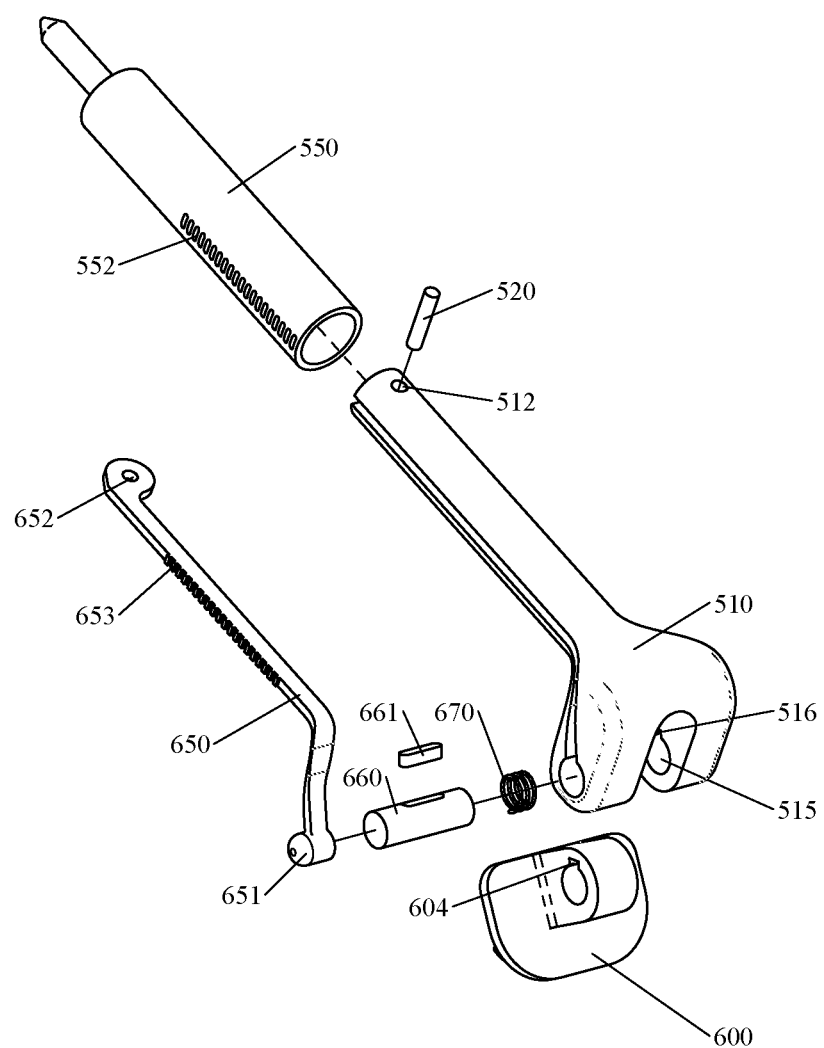
FIG. 22 is an exploded perspective view of an alternative embodiment of the invention.
Figure 23:
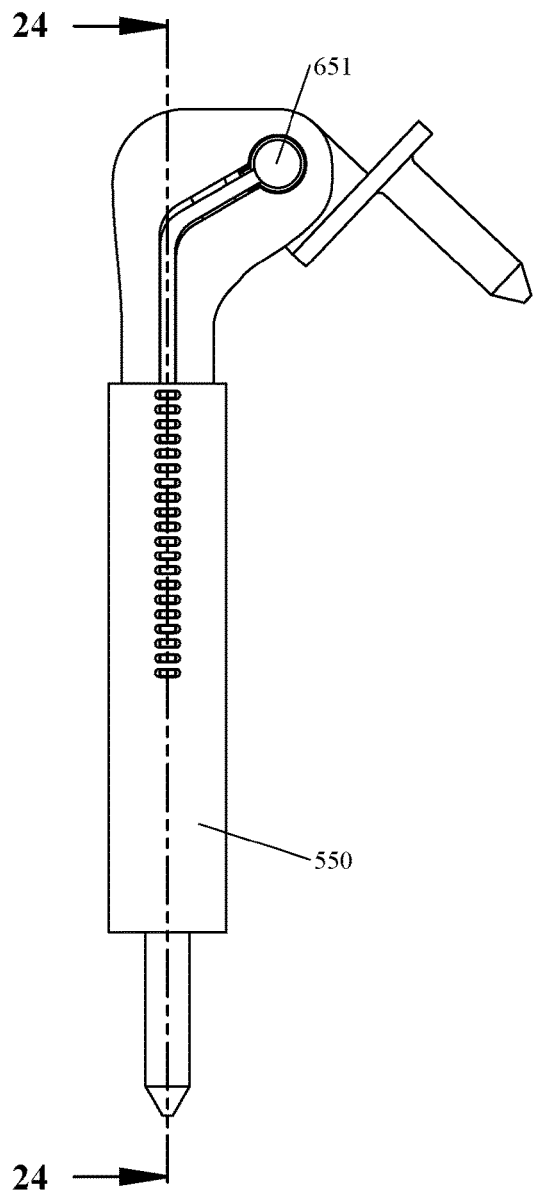
FIG. 23 is a side view of an alternative embodiment of the invention.
Figure 24:
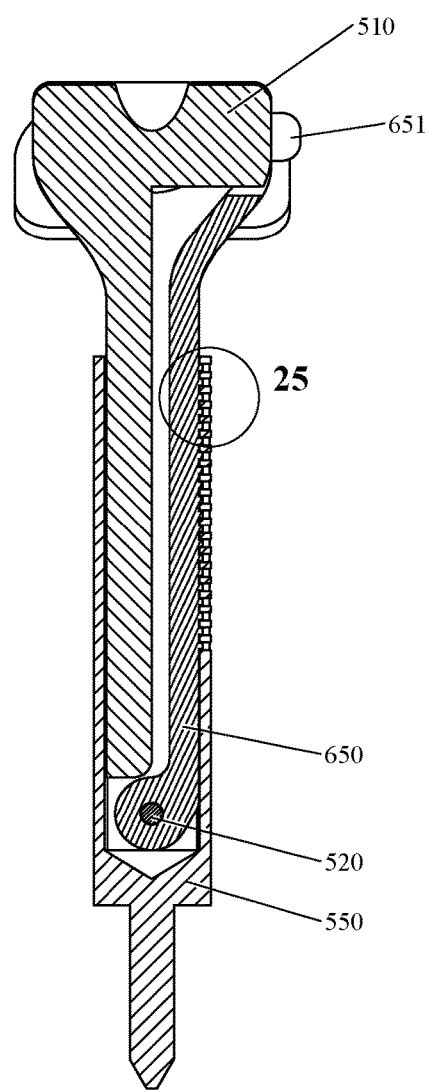
FIG. 24 is a sectional view of an alternative embodiment of the invention, shown in a locked configuration.
Figure 25:
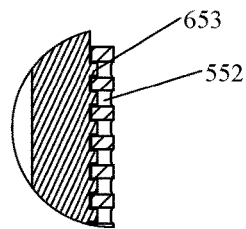
FIG. 25 is an enlarged sectional view of an alternative embodiment of the invention, illustrating the locked configuration.
Figure 26:
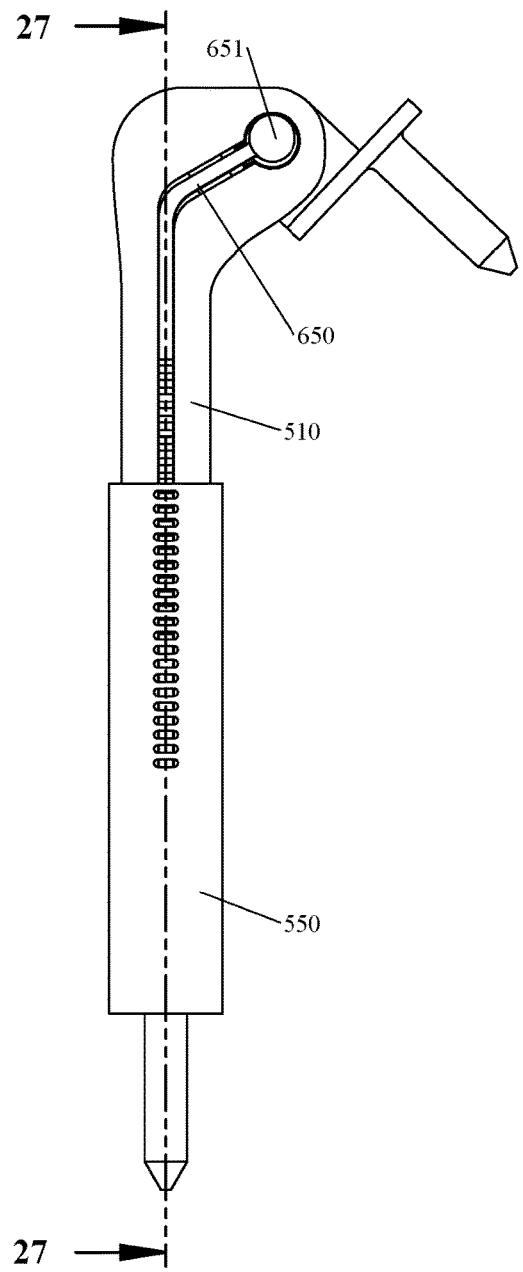
FIG. 26 is a side view of an alternative embodiment of the invention, shown in an unlocked and lengthened configuration.

FIG. 20 is an alternative embodiment of the invention configured to replace the proximal tibia. The invention here works in the same way as described for previous embodiments. A shaft 340 is palpated at the location of the patient's knee and pressed back and forth to lengthen the implant, just as previously described in the preferred embodiment.

Figure 27:
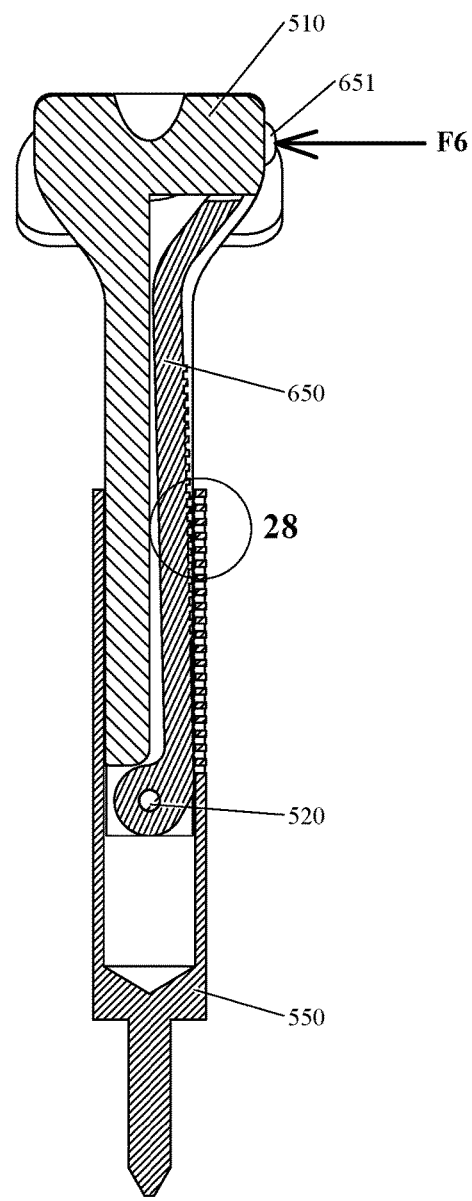
FIG. 27 is a sectional view of an alternative embodiment of the invention, shown in an unlocked and lengthened configuration.
Figure 28:
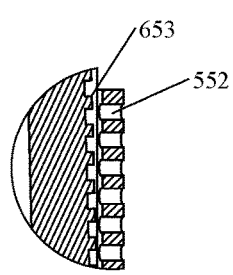
FIG. 28 is an enlarged sectional view of an alternative embodiment of the invention, illustrating the unlocked configuration.
Figure 29:
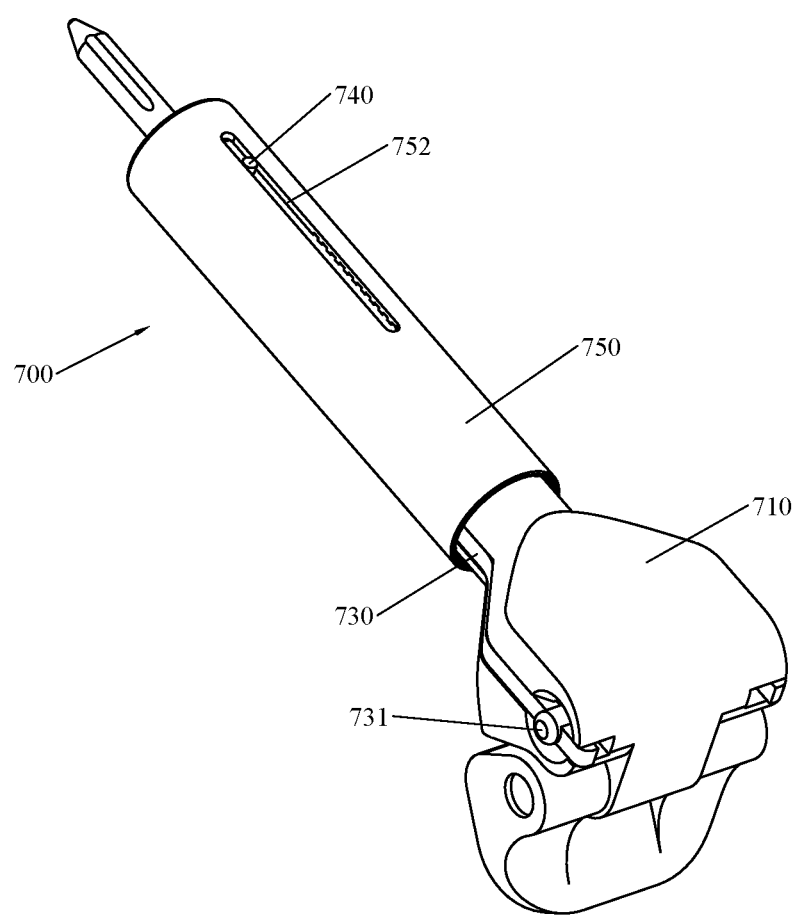
FIG. 29 is a perspective view of an alternative embodiment of the invention.
Figure 30:
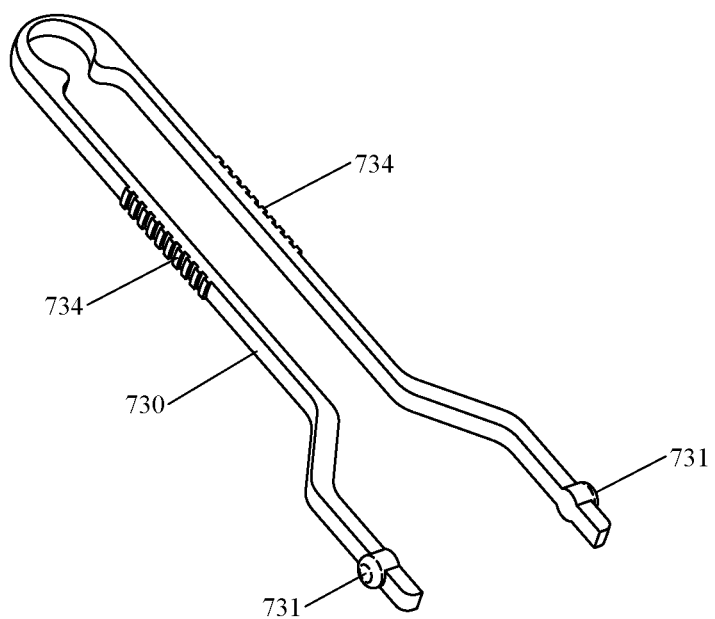
FIG. 30 is a perspective view of the locking mechanism of an alternative embodiment of the invention.
Figure 31:
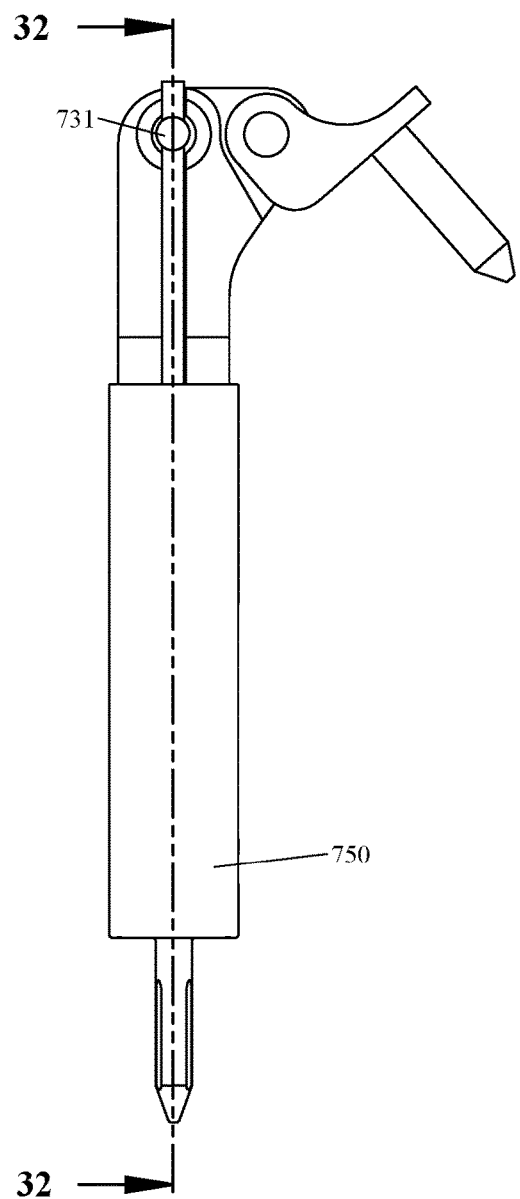
FIG. 31 is a side view of an alternative embodiment of the invention.
Figure 32:
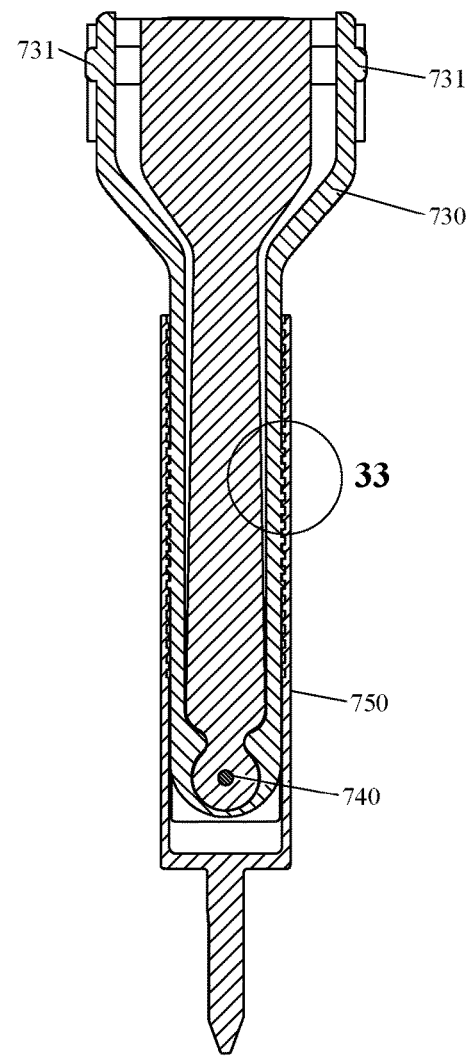
FIG. 32 is a sectional view of an alternative embodiment of the invention, shown in a locked configuration.
Figure 33:
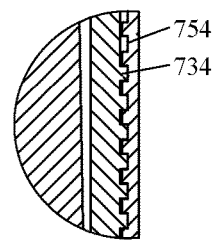
FIG. 33 is an enlarged sectional view of an alternative embodiment of the invention, illustrating the locked configuration.
Figure 34:
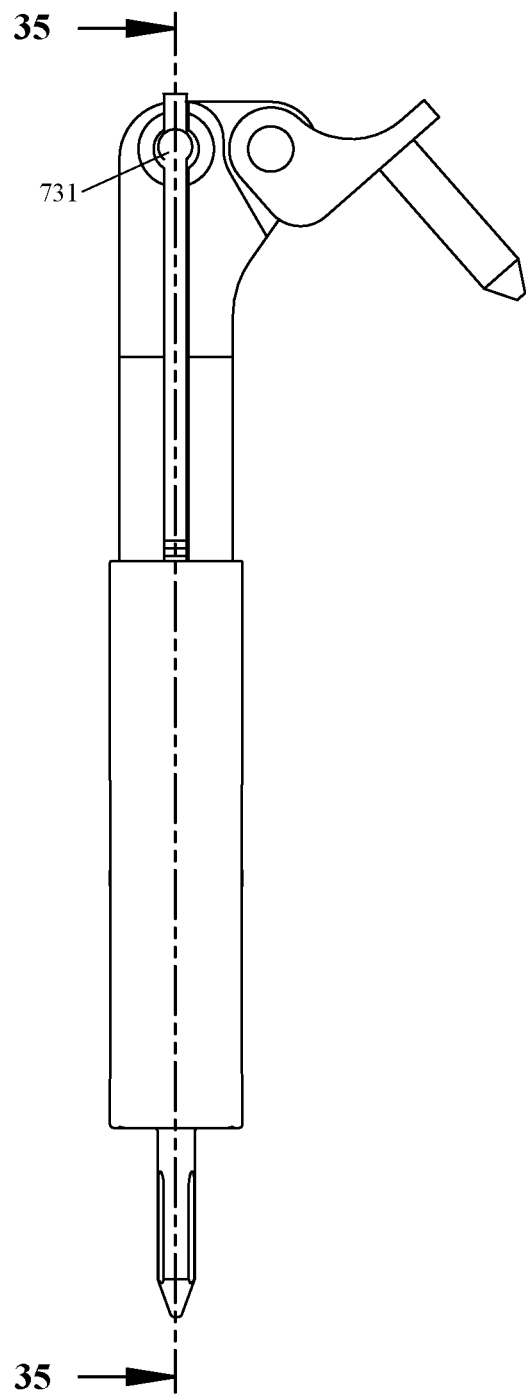
FIG. 34 is a side view of an alternative embodiment of the invention, shown in an unlocked and lengthened configuration.

FIGS. 21 through 28 illustrate an alternative embodiment 500 of the invention wherein the implant can be lengthened by (1) pressing on a button located beneath the skin to unlock the implant, (2) pulling the patient's leg to the desired length, and (3) releasing the button to lock the implant at the new length. The configuration shown of this alternative embodiment of the invention is for replacement of the distal femur, similar to the preferred embodiment. A locking bar 650 has a plurality of teeth 653 which engage in slots 552 in femoral shaft component 550, locking the implant's length. Alternatively, slots 552 could be radial grooves, partial radial grooves or a square female thread. Locking bar 650 incorporates a button 651 which can be palpated by pushing on the patient's skin. Pressing button 651 rotates locking bar 650 about the hinge created by a pin 520 which passes through a hole 512 in distal femur component 510, and a hole 652 in locking bar 650. Axle 660, located in a blind bore 515 within distal femoral component 510, is able to translate further into blind bore 515 due to compression of spring 670. As locking bar 650 rotates, teeth 653 disengage from slots 552, thereby unlocking distal femur component 510 from femoral shaft component 550 as shown in FIGS. 27 & 28. When these components are unlocked distal femur component 510 is free to slide into or out of femoral shaft component 550 thereby allowing the length of the implant to be increased or decreased. Axle 660 is rotationally restricted relative to tibial component 600 by the engagement of a key 661 in keyway 604 in tibial component 600. To prevent inadvertent unlocking of the components, the knee must be rotated to an unlocked position whereby keyway 604 in tibial component 600 aligns with keyway 516 in femoral component bore 515 so that shaft 660 can translate and compress spring 670. Therefore the implant can only be unlocked when the patient's knee is in a particular rotational orientation. The unlocked position can be any rotational orientation, and the rotational locations of keyway 516 and keyway 604 can be created to reflect that preference. Once the implant is unlocked the patient's limb can be manually manipulated by the operator performing the adjustment. When the intended length is achieved, the operator removes their force F6 on button 651 allowing locking bar 650 to return to its locked position.

Figure 35:
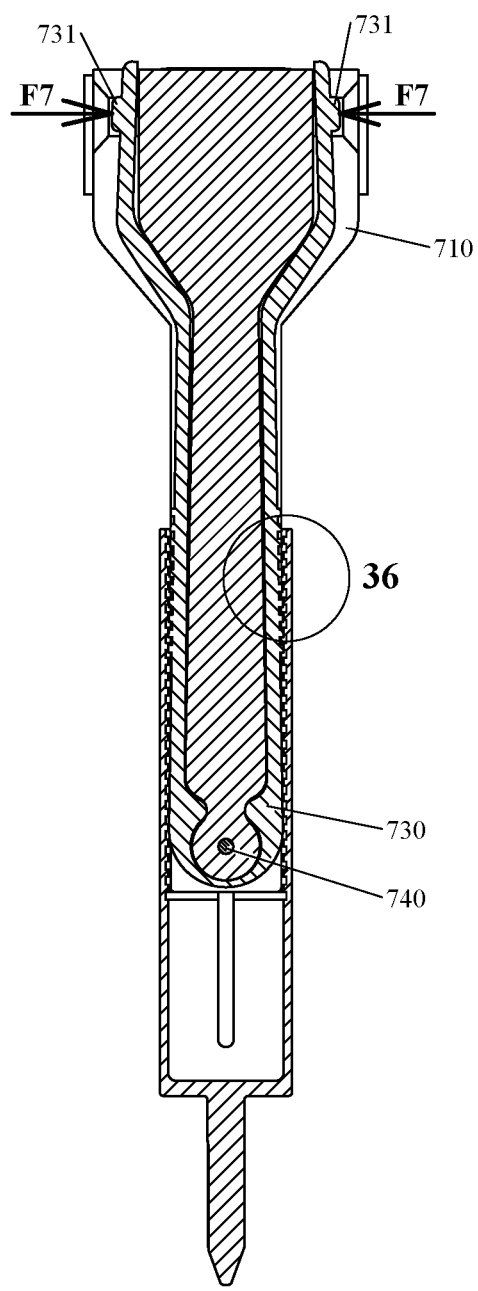
FIG. 35 is a sectional view of an alternative embodiment of the invention, shown in an unlocked and lengthened configuration.
Figure 36:
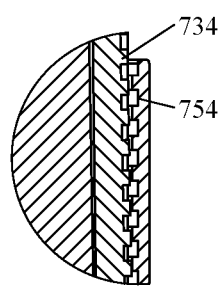
FIG. 36 is an enlarged sectional view of an alternative embodiment of the invention, illustrating the unlocked configuration.

The alternative embodiment 700 depicted in FIGS. 29 through 36 includes a flexible locking bar 730 which functions similarly to locking bar 650. No spring is necessary due to the spring action of flexible locking bar 730. In this embodiment it is necessary to compress flexible locking bar 730 by pressing with a force F7 as shown in FIG. 35 on buttons 731 on both lateral and medial sides of the patent's knee to disengage teeth 734 from grooves 754 located inside femoral shaft component 750. A pin 740 rides in a slot 752 in femoral shaft component 750 to maintain the rotational orientation and limit the travel of distal femur component 710 within femoral shaft component 750. Although no lock-out is depicted requiring the knee to be in a particular rotational orientation (as described in the preferred embodiment) it can be assumed that such a lockout mechanism could be incorporated in this embodiment.

The invention claimed is:

1. A non-invasively extendable endoprosthesis incorporating: a first feature configured for attachment to a first long bone, a second feature configured for attachment to a second, adjacent long bone, a joint having at least one rotational degree of freedom which is intended to replace the function of an orthopaedic joint, and a lengthening mechanism which is purely mechanical and manually operates while being located and activated by an operator post-operatively by pressing on skin of the patient, without requiring a surgical incision, a magnet, a hydraulic or pneumatic component, electrical current or application of heat.

2. The endoprosthesis according to claim 1, wherein said joint is designed to replace a knee joint.

3. The endoprosthesis according to claim 1, wherein said joint is designed to replace an elbow joint.

4. A The endoprosthesis according to claim 1, wherein said lengthening mechanism comprises a one-way clutch.

5. A The endoprosthesis according to claim 1, wherein said lengthening mechanism comprises a one-way bearing.

6. A The endoprosthesis according to claim 1, wherein said lengthening mechanism comprises a leadscrew.

7. A The endoprosthesis according to claim 1, wherein said lengthening mechanism comprises a ratchet and pawl.

8. A The endoprosthesis according to claim 1, wherein said lengthening mechanism comprises a rack and pinion.

9. A The endoprosthesis according to claim 1, wherein said lengthening mechanism utilizes a mechanical lockout device which deters inadvertent lengthening by requiring that said joint be in a particular orientation in order for lengthening to occur.

10. The endoprosthesis according to claim 1, wherein at least one of said first feature and said second feature utilizes an intramedullary stem which is meant to be inserted into the intramedullary canal of a said first long bone or said second, adjacent on bone for the purpose of attachment of the invention to the patient.

11. A non-invasively extendable endoprosthesis incorporating a first feature configured for attachment to a first long bone, a second feature configured for attachment to a second, adjacent long bone, a joint having at least one rotational degree of freedom which is intended to replace the function of an orthopaedic joint, and a release mechanism which is purely mechanical and manually operates while being located and activated by an operator post-operatively by pressing on skin of a patient, without requiring a surgical incision, a magnet, a hydraulic or pneumatic component, electrical current or application of heat, wherein said operator may subsequently pull or push the limb to change its length.

12. The endoprosthesis according to claim 11, wherein said joint is designed to replace a knee joint.

13. The endoprosthesis according to claim 11, wherein said joint is designed to replace an elbow or joint.

14. A The endoprosthesis according to claim 11, wherein said release mechanism incorporates a plurality of teeth.

15. A The endoprosthesis according to claim 11, wherein said release mechanism utilizes a mechanical lockout device which deters inadvertent lengthening by requiring that said joint be in a particular rotational orientation in order for lengthening to occur.

16. The endoprosthesis according to claim 11, wherein said first feature, said second feature, or both said first and said second features comprise an intramedullary stem which is meant to be inserted into the intramedullary canal of said first long bone or said second, adjacent long bone for the purpose of attachment of the invention to the patient.

* * * * *